(12) United States Patent
Chan (10) Patent No.: US 6,948,209 B2
(45) Date of Patent: Sep. 27, 2005

(54) ELECTRIC TOOTHBRUSHES HAVING FLEXIBLE NECKS

(75) Inventor: John Geoffrey Chan, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/659,489

(22) Filed: Sep. 10, 2003

(65) Prior Publication Data

US 2004/0128780 A1 Jul. 8, 2004

Related U.S. Application Data

(60) Provisional application No. 60/410,864, filed on Sep. 13, 2002, and provisional application No. 60/410,902, filed on Sep. 13, 2002.

(51) Int. Cl.[7] .......................... A46B 13/02; A61C 17/16
(52) U.S. Cl. .............................. 15/22.1; 15/22.2; 15/28
(58) Field of Search ................................. 15/22.1, 22.2, 15/23, 28

(56) References Cited

U.S. PATENT DOCUMENTS

| | | | |
|---|---|---|---|
| 2,911,660 A | * | 11/1959 | Klemas et al. ................. 15/28 |
| 3,115,652 A | | 12/1963 | Zerbee |
| 3,509,874 A | | 5/1970 | Stillman |
| 4,845,796 A | | 7/1989 | Mosley |
| 5,732,432 A | | 3/1998 | Hui |
| 5,784,742 A | | 7/1998 | Giuliani et al. |
| 5,901,397 A | | 5/1999 | Hafele et al. |
| 6,000,083 A | | 12/1999 | Blaustein |
| 6,092,252 A | * | 7/2000 | Fischer et al. ................ 15/22.1 |
| 6,230,717 B1 | * | 5/2001 | Marx et al. .................. 132/308 |
| 6,802,097 B2 | * | 10/2004 | Hafliger et al. .............. 15/22.1 |

FOREIGN PATENT DOCUMENTS

| | | |
|---|---|---|
| GB | 2036551 A | 7/1980 |
| JP | 7-116028 A | 7/1994 |
| WO | WO 95/20365 | 8/1995 |
| WO | WO 01/29128 | 4/2001 |
| WO | WO 03/030680 | 4/2003 |

OTHER PUBLICATIONS

U.S. Appl. No. 10/110,913, filed Apr. 17, 2002, Wang.

* cited by examiner

Primary Examiner—Randall Chin
(74) Attorney, Agent, or Firm—James C. Vago; Richard L. Alexander (57) ABSTRACT

An electric toothbrush is disclosed having a flexible neck. Particular degrees of lateral, rearward, and forward flexibility of a brush head with respect to the handle of the toothbrush are achieved by utilizing polymer blends.

24 Claims, 9 Drawing Sheets

ELECTRIC TOOTHBRUSHES HAVING FLEXIBLE NECKS

This application claims the benefit of U.S. Provisional Application No. 60/410,864, filed Sep. 13, 2002, and U.S. Provisional Application No. 60/410,902, filed Sep. 13, 2002, the substance of which is incorporated herein by reference.

FIELD OF THE INVENTION

The present invention relates to the field of electric toothbrushes, and particularly, to electric toothbrushes having flexible necks.

BACKGROUND OF THE INVENTION

Flexible neck toothbrushes are known in the art. Flexible necks can increase brushing efficacy since the brush head may be better oriented to specific relationships with a user's teeth and gums. Secondly, if appropriately configured, a flexible neck may limit the amount of force applied to the teeth and gums during brushing. It is documented that excessive brushing force can be deleterious to the user's teeth and gums.

Traditionally, electric toothbrushes utilize a relatively rigid hollow neck. This is primarily due to the fact that a moving drive mechanism resides within the handle and neck portion of the toothbrush. In an alternate arrangement, U.S. Pat. No. 4,845,796 discloses an electric toothbrush having a rotating flexible stem that frictionally engages a motor. The rotating flexible stem is not disposed within a neck structure that is separately attached to the handle of the electric toothbrush. While the prior designs may have been suitable for their intended purpose, there is a continuing need to provide electric toothbrushes having flexible necks that can accommodate bristle carriers that move in other and more complex motions. Further, there is a desire to provide electric toothbrushes having flexible neck that can include static as well as moving bristles. Still further, there is a desire to provide electric toothbrushes having flexible necks in which the direction and amount of flexure can be controlled. Yet further, there is a continuing desire to provide electric toothbrushes having flexible necks that have simplified constructions.

SUMMARY OF THE INVENTION

An electric toothbrush is provided. The electric toothbrush includes a handle having an interior cavity, a head, and a flexible neck extending between the handle and the head. The head has a movable bristle carrier that is driven by a motor disposed within the cavity of the handle. A shaft is disposed within the flexible neck that is operatively connected to the movable bristle carrier and to the motor.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

DETAILED DESCRIPTION OF THE PREFERRED EMBODIMENTS

Figure 2:
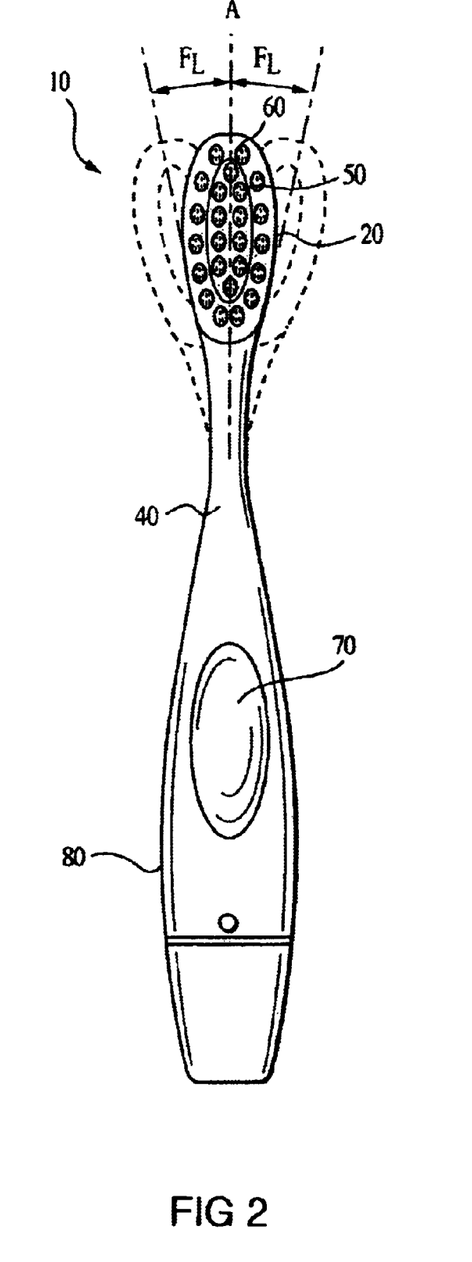
FIG. 2 is a front elevational view of the toothbrush of FIG. 1.
Figure 3:
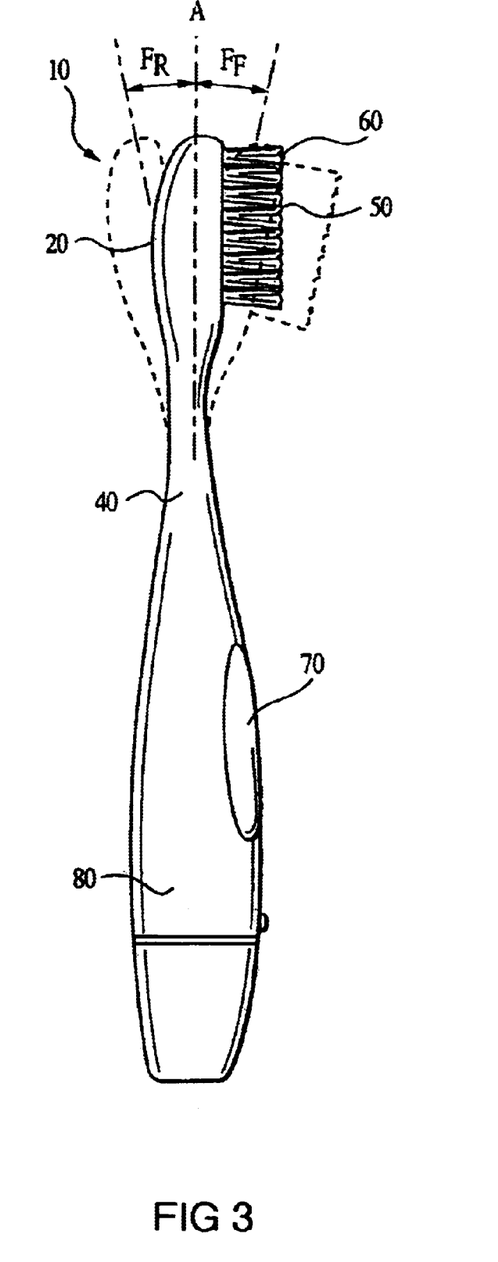
FIG. 3 is a side elevational view of the toothbrush of FIG. 1.

All patents, patent publications, ASTM and ISO standards referenced herein, including U.S. Provisional Application No. 60/410,864, filed Sep. 13, 2002, and U.S. Provisional Application No. 60/410,902, filed Sep. 13, 2002 are incorporated herein by reference. The electric toothbrushes of the present invention incorporate a neck that is flexible and resilient, meaning that at least a portion of the neck can assume a curved or curvilinear shape or otherwise bend when a tooth brushing force is applied to the toothbrush head. This deflection can occur over the entire neck or only a portion thereof, such as shown in FIGS. 2 and 3. It will be appreciated that the neck can assume a curved shape having a single radius of curvature or multiple radii of curvature. Further, it will be appreciated that the present invention can be adapted to an electric toothbrush head to provide a flexible head. The flexible neck can be achieved by forming the neck from a mixture of polymers or varying the cross-sectional shape of the neck in combination with the appropriate polymer or blend of polymers.

By utilizing a mixture of polymers in the neck, various degrees of flexibility in the region of the neck may be achieved. Preferably, the polymer mixture is a blend of a first polymer with a second polymer that has a lower flexural modulus, i.e., that is generally more flexible, than the first polymer. Additionally and preferably, the hardness of the second polymer is less than that of the first polymer. Specifically, the Shore A hardness of the second polymer is preferably from about 25 to about 85. Standards for determining Shore A hardness are set forth in ASTM D 2240 and the standards for determining flexural modulus are set forth in ASTM D790 and ISO 178.

Preferably, the weight ratio of the first polymer to the second polymer is from about 95:5 to about 30:70. It is believed that this ratio is dependent on the hardness of the second polymer material. For example, for the following Shore A hardness ranges of the second polymer, the corresponding ratios of the first polymer to the second polymer are preferred. For a Shore A hardness of from about 25 to about 45, the preferred weight ratio of the first polymer to the second polymer is from about 90:10 to about 60:35, with from about 85:15 to about 65:35 being more preferred. For a Shore A hardness of from about 45 to about 65, the preferred weight ratio of the first polymer to the second polymer is from about 80:20 to about 50:50, with from about 75:25 to about 55:45 being more preferred. For a Shore A hardness of from about 65 to about 85, the preferred ratio of the first polymer to the second polymer is from about 70:30 to about 40:60, with from about 65:35 to about 45:55 being more preferred.

In the following description of the preferred polymer materials for use herein, the abbreviations that are commonly used by those of skill in the art to refer to certain polymers appear in parentheses following the full names of the polymers. The first polymer is preferably polypropylene ("PP"), or may be selected from the group consisting of other conventional toothbrush handle materials, such as polystyrene ("PS"), polyethylene ("PE"), acrylonitrile-styrene copolymer ("SAN"), cellulose acetate propionate ("CAP"), and mixtures thereof. The second polymer is preferably a thermoplastic elastomer ("TPE"), a thermoplastic olefin ("TPO"), a soft thermoplastic polyolefin (e.g., polybutylene), or may be selected from other elastomeric materials, such as ethylene-vinylacetate copolymer ("EVA"), ethylene propylene rubber ("EPR"), and mixtures thereof. Examples of suitable thermoplastic elastomers herein include styrene-ethylene-butadiene-styrene ("SEBS"), styrene-butadiene-styrene ("SBS"), and styrene-isoprene-styrene ("SIS"). Examples of suitable thermoplastic olefins herein include polybutylene ("PB"), and polyethylene ("PE").

For toothbrushes, the handle and the head are commonly joined via a neck area, which as noted above may be of a smaller cross-sectional area than the handle or the head. The head is provided with apertures for receiving bristles or bundles of bristles, which are mechanically or thermally fixed therein, as is known to those of skill in the art. Any such method for fixing the bristles can be used herein.

Figure 1:
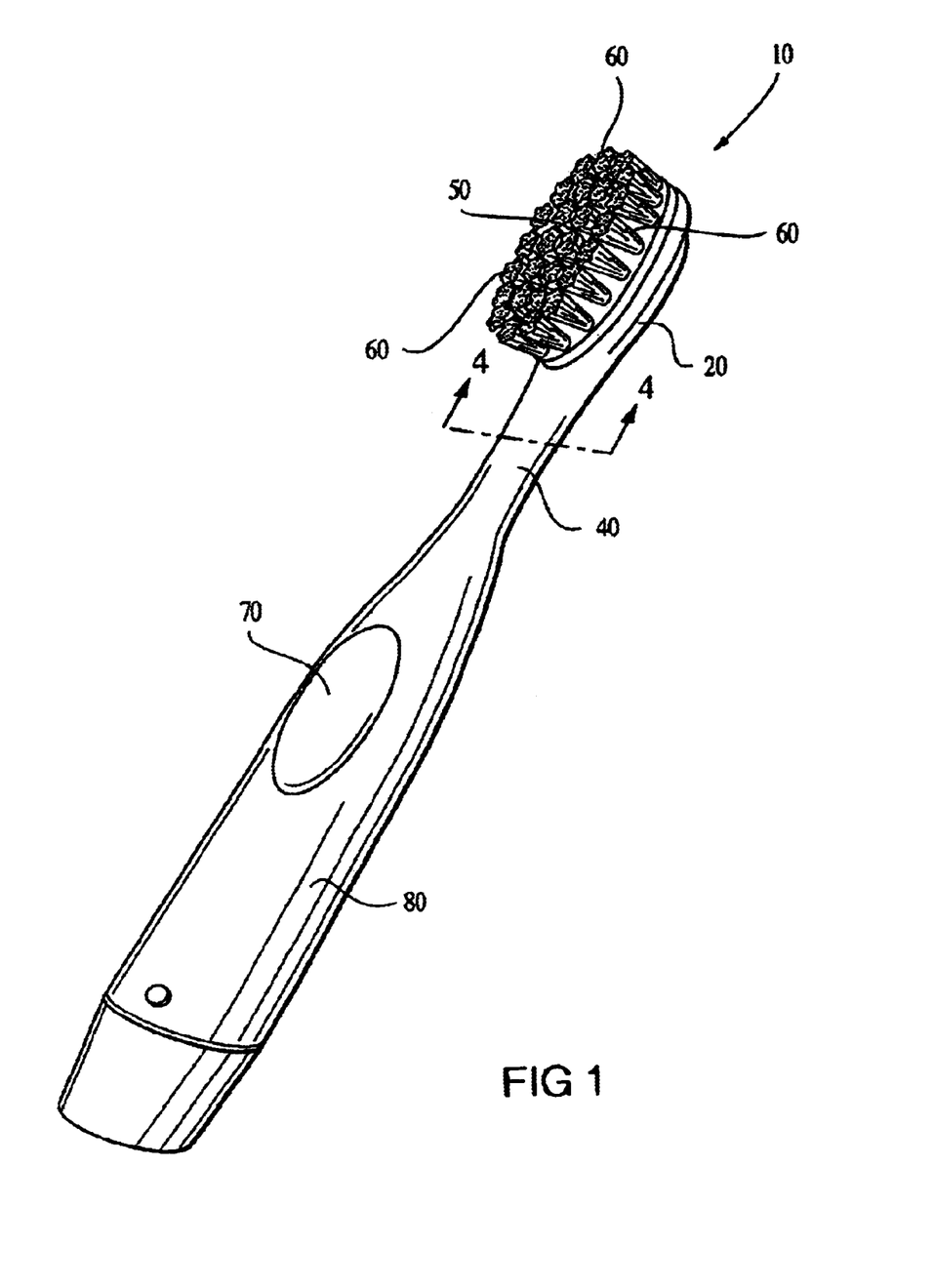
FIG. 1 is a perspective view of a toothbrush made in accordance with the present invention.

FIG. 1 is a perspective view illustrating a preferred embodiment toothbrush 10 according to the present invention. The preferred embodiment toothbrush 10 comprises a handle 80, a head 20, and a neck 40 extending between the handle 80 and the head 20. Disposed on the head 20 are a plurality of stationary bristles 60 and a plurality of movable bristles 50. A number of bristle types, configurations, and arrangements may be used for the bristles. Examples of such aspects are disclosed and taught in the previously noted patents and furthermore in U.S. Design Pat. 432,312; and 433,814. Most preferably, the movable bristles 50 are supported or otherwise secured to a movable bristle carrier (not shown) that is retained on the brush head 20. As will be appreciated, the movable bristle carrier and the movable bristles 50 are powered by a motor and drive train or mechanism disposed in a hollow interior cavity defined within the body, i.e. the handle 80 of the toothbrush 10. A switch or actuator 70 is provided along the outer region of the handle 80 and is operatively connected to the motor and drive train and is used to control operation of the electric toothbrush 10.

FIGS. 2 and 3 illustrate front and side elevational views, respectively, of toothbrush 10 shown in FIG. 1. It can be seen from these figures that the flexible neck 40 allows reversible or resilient lateral, rearward, and forward displacement of the head 20 with respect to the handle 80. The term "reversible" as used herein refers to the ability of the toothbrush to be displaced in the noted direction and to the noted extent, without breakage or fracture of the toothbrush body or neck, and then to return to its previous state or orientation. Specifically, in accordance with the present invention, the degree of reversible lateral displacement of the head with respect to the longitudinal axis of the electric toothbrush is approximately from about 25 degrees to about 5 degrees and preferably from about 15 degrees to about 10 degrees. It is preferred that this flexibility or range of lateral displacement is equivalent for both lateral directions of movement of the brush head relative to the handle. Referring to FIG. 2, this degree of movement is illustrated and shown as lateral flexure $F_L$. That is, it can be seen from FIG. 2, that the brush head 20 may be laterally displaced by an amount of flexure shown as $F_L$ with respect to the longitudinal axis of the toothbrush when in a non-flexing or displaced state. The longitudinal axis of the toothbrush is shown in these figures as axis A.

Similarly, as noted, the toothbrush 10 may also undergo reversible rearward and forward flexure of the brush head with respect to the handle. This is shown in FIG. 3. The preferred amount of reversible rearward flexure, shown in FIG. 3 as $F_R$, ranges from about 15 degrees to about 5 degrees. The preferred amount of reversible forward flexure, shown in FIG. 3 as $F_F$, ranges from about 15 degrees to about 5 degrees.

The previously noted flexures, i.e. $F_L$, $F_R$, and $F_F$, result from application of a force to either the handle 80 or to the brush head 20. The neck 40 is sufficiently flexible so that only a relatively slight force is necessary to achieve the noted flexures. The following ranges of force are given with regard to application of the force at the center of the brush head 20, in the appropriate direction to result in the noted flexure. A lateral flexure $F_L$ of from about 25 degrees to about 5 degrees, for the toothbrush 10, results from application of a force between about 4 N or about 10 N to about 10 N or about 20 N, along a side of the brush head 20. A rearward flexure $F_R$ of from about 15 degrees to about 5 degrees results from application of a force between about 4 N or about 8 N to about 8 N or about 20 N along the front or bristle-containing face of the brush head 20. A forward flexure $F_F$ of from about 15 degrees to about 5 degrees results from application of a force between about 4 N or about 8 N to about 8 N or about 20 N along the rear or back face of the brush head 20. A wide range of ratios of displacement to force are achievable by utilizing different types and blends of polymers in the neck or body of the toothbrush and different structures and dimensions of the neck and body.

The sample brushes were tested as follows. The test apparatus comprised a tensile tester (<100 N), steel wire, and brush handle clamper.

The test samples were prepared by marking the samples with two marks. The first mark is made at 15 mm from the top of the brush head and the second mark is made at 80 mm from the top of the brush head. The samples were prepared at a temperature of 20°+/−5° C., and this temperature is kept constant for four hours prior to start of the testing procedure.

The test procedure is as follows. A steel wire was folded having a diameter of about 2 mm and a length of about 250 mm and placed into the upper clamper of the tester. The brush handle was put into the brush handle gripper and fixed on the position of the second mark (with the brush bristles downward). The brush handle gripper was connected to the lower clamper of the tester and the steel wire placed on the position of the first mark. The tester was started up and the reading was taken when the sample was bent to 25 mm or broken. The result was measured in Newtons (N).

The testing conditions were ambient temperature maintained at 20°+/−5° C. The rising up and dropping down speed of the tester was kept constant at 100+10 mm/min. In addition, the tensile tester was calibrated using a confirmed standard sample, or equipment manufacturer's calibration procedure.

The degree of flexibility of a sample is indicated in that a flexible sample is more easily deformed as compared to a relatively more rigid sample.

That is, the lower the amount of force needed to bend or break a brush, the more flexible the brush is. Therefore, lower values of N indicate greater flexibility.

Figure 4:
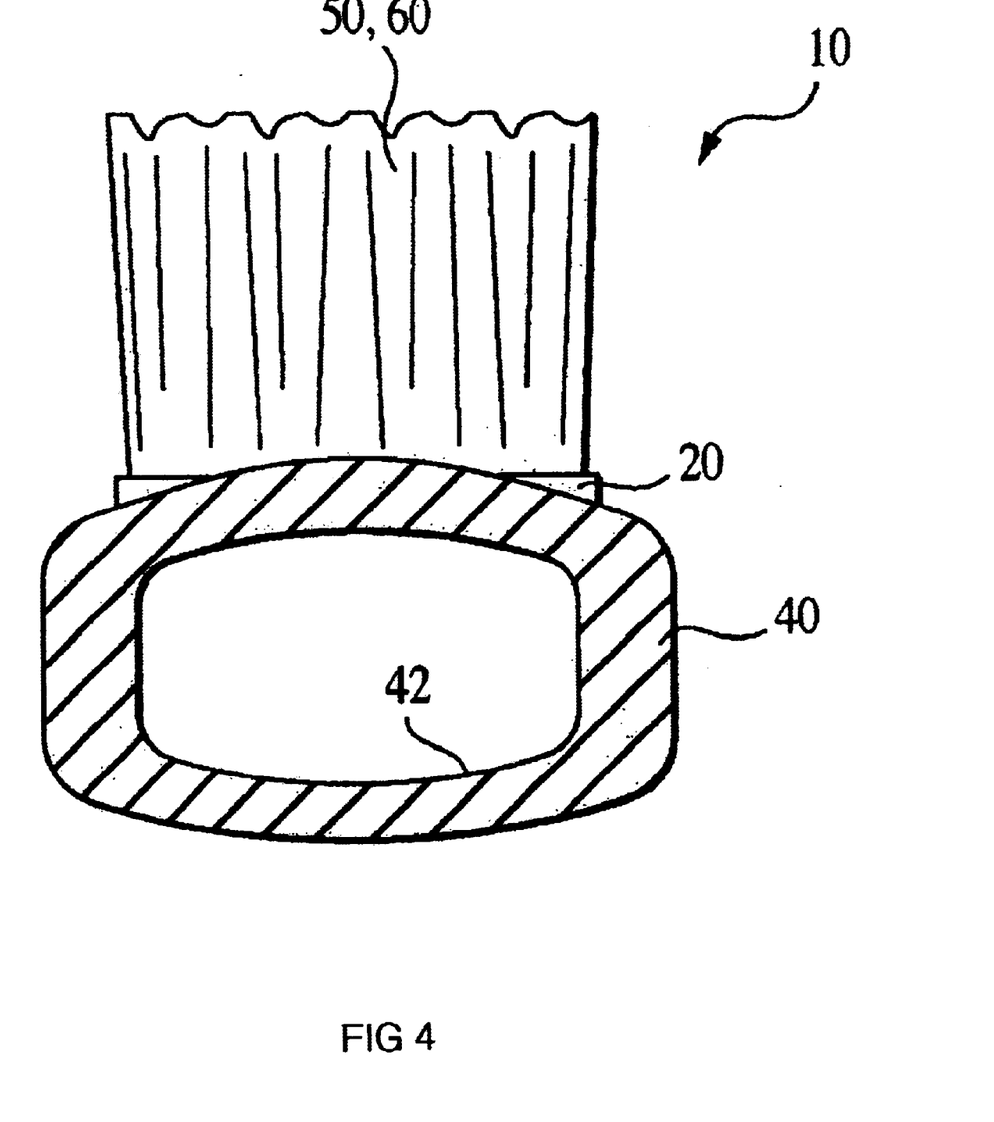
FIG. 4 is a cross-sectional view of a neck of the toothbrush of FIG. 1, taken along line 4—4 in FIG. 1.

FIG. 4 is a detailed cross-sectional view of the toothbrush 10 taken across line 4—4 in FIG. 1. FIG. 4 reveals a hollow channel defined by an interior neck channel wall 42. The interior configuration of this channel may be in a variety of forms. However, it is preferred that a generally rectangular or oval shape is preferred. The shape or configuration of the interior channel within the neck 40 is defined by an interior wall 42 as shown in FIG. 4. It will be appreciated that one or more components of the drive mechanism extend and reside within this interior channel defined by wall 42. Most preferably, a shaft or ribbon is disposed within the channel that undergoes reciprocating, rotating or oscillating motion upon activation of the motor. The size and configuration of the interior channel is preferably such that the wall 42 is in relatively close proximity to the outer surface of these components, however, a sufficient distance apart from these components during flexure of the neck so that contact does not occur between the wall 42 and component(s). In the event that contact occurs, it is contemplated that a friction reducing coating could be applied to the wall 42, the exterior of the drive components, or both.

Figure 5:
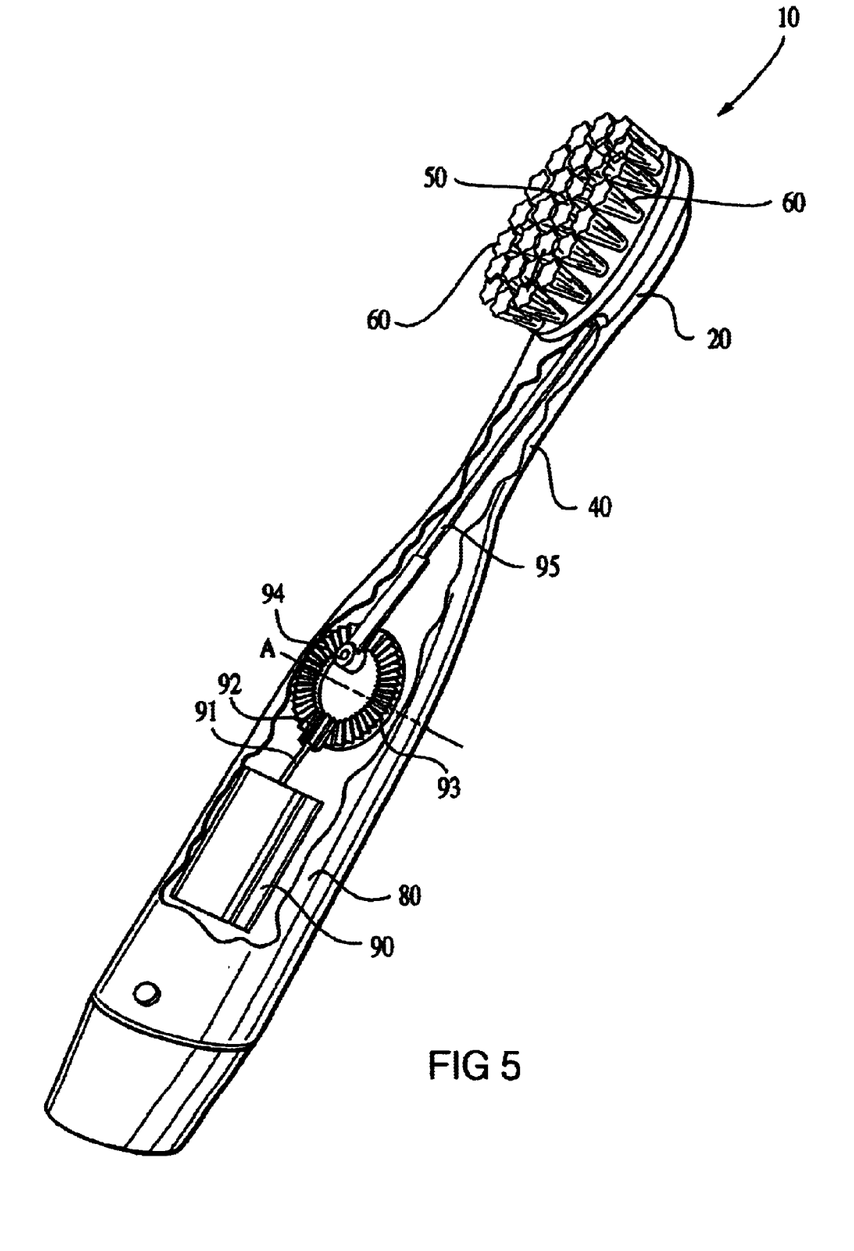
FIG. 5 is a partial fragmentary perspective view of the toothbrush of FIG. 1.

A preferred drive mechanism is illustrated in FIGS. 5 to 9, wherein a drive mechanism incorporating a flexible shaft or ribbon is illustrated. FIG. 5 is a partial fragmentary view of the preferred embodiment toothbrush 10 shown in FIG. 1. FIG. 5 illustrates a motor 90 and a drive train or mechanism retained within the handle 80 that are used to move the collection of movable bristles 50 disposed on the brush head 20. The movable bristles are attached to and supported by a movable bristle carrier. Upon activation of a switch or actuator 70 (shown in FIG. 1) disposed along the handle 80 of the toothbrush 10, electrical energy such as from one or more batteries in the housing 80, is directed to a motor 90. The motor 90 includes a drive shaft 91 to which is affixed a drive gear 92. The drive gear 92 is engaged with a rotatable drive gear 93. The drive gear 93 is mounted such that it rotates about an axis A preferably extending in a direction perpendicular to the drive shaft 91 of the motor. The drive gear 93 includes a pin or drive member 94 which is disposed on the drive gear 93 radially outward from the center of rotation, or axis A, of the drive gear 93. Attached to the drive member 94 is a drive ribbon 95. This arrangement of drive components imparts reciprocating motion to the drive ribbon 95 from a powered rotary drive shaft 91. As will be appreciated, other gearing arrangements can be provided between the motor 90 and the ribbon 95. For example, various drive mechanisms described in U.S. Pat. Nos. 6,178,579; 6,189,693; 6,360,395; and 6,371,294 might be adapted or utilized.

Figures 6, 7, 8:
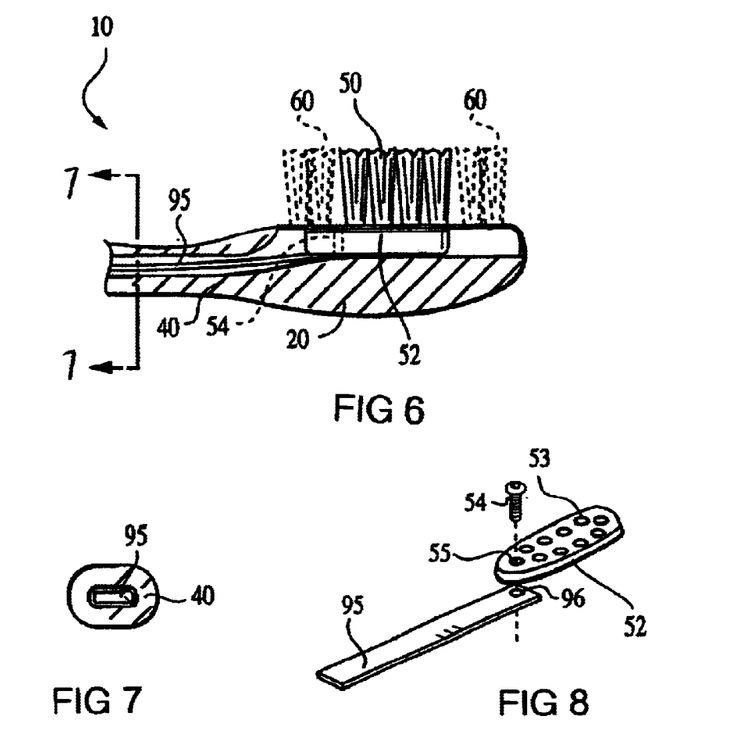
FIG. 6 is a side elevational view of the toothbrush of FIG. 5.
FIG. 7 is a cross-sectional view taken along line 7—7 of FIG. 6.
FIG. 8 is a partial exploded view of a movable bristle carrier and drive shaft of the toothbrush of FIG. 5.

FIGS. 6 to 8 illustrate the configuration and engagement of the distal end of the drive ribbon 95 to a movable bristle carrier 52 disposed on or within the head 20. Specifically, the distal end of the drive ribbon 95 extends through a channel defined within the neck 40 as shown in FIGS. 6 and 7, and is exposed or otherwise accessible in the region of the head 20. The movable bristle carrier 52 is movably retained along the brush head 20, such as within a channel or slot defined in one or more faces of the head. As shown in FIG. 8, the movable bristle carrier 52 is engaged to the distal end of the drive ribbon 95 by a pin 54. It will be appreciated that other types of engagement may be used between the carrier 52 and the ribbon 95. Preferably, the pin 54 is positioned through an aperture 55 defined in the movable bristle carrier 52, and further positioned within an aperture 96 defined in the end of drive ribbon 95. As will be appreciated, the bristle carrier 52 supports and retains a collection of bristles or bristle tufts within one or more apertures 53.

Figure 9:
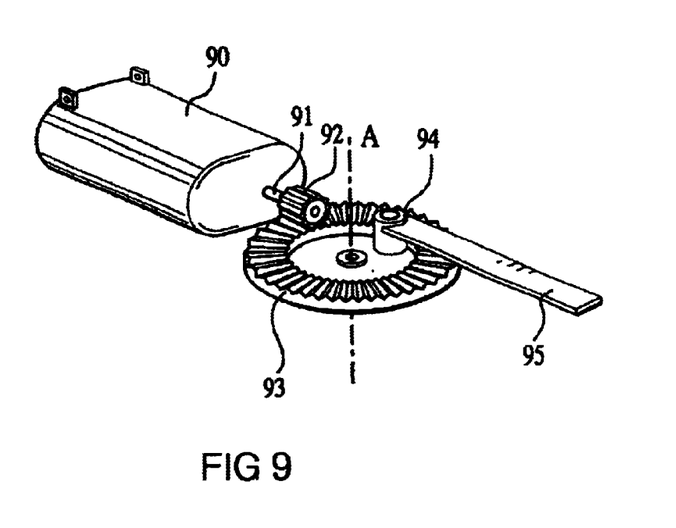
FIG. 9 is a perspective view of a motor and drive train suitable of the toothbrush of FIG. 5.

FIG. 9 illustrates in greater detail, a preferred configuration for the engagement between the motor 90 and the drive ribbon 95. Specifically, this configuration imparts a reciprocating motion to the drive ribbon 95 upon actuation of the motor 90. The drive gear 92 is engaged with the rotatable drive gear 93 such that upon operation of the motor 90, the drive gear 93 is rotated about axis A. As can be seen in FIG. 9, the drive gear 93 includes a drive member 94 to which is engaged an end of the drive ribbon 95. The drive member 94 is located off-center, or radially outward, from the axis of rotation A of the drive gear 93. The engagement between the drive member 94 and the drive ribbon 95 enables angular or pivotal movement of drive ribbon 95 at the point of attachment of drive member 94. Rotation of the drive gear 93 imparts a reciprocating motion to the drive ribbon 95 as a result of the location of the drive member 94 relative to the axis of rotation A of the drive gear 93. The stroke of the reciprocating movement imparted to the drive member 95 can be increased by locating the drive member 94 radially outward and further away from the axis of rotation A of the drive gear 93. And, the stroke may be decreased by locating the drive member 94 closer to the axis of rotation A. The frequency of the reciprocating movement is adjusted by changing the rate of rotation of the drive gear 93. This may be accomplished by modifying the gearing relationship between gears 92 and 93, or by providing a different rate of rotation of the motor 90 and drive shaft 91.

Upon operation of the motor 90, it will be appreciated that a lateral component of movement will also be imparted to the drive ribbon 95, in addition to a reciprocating component of movement. These descriptions of motion are with respect to the longitudinal axis of the drive ribbon 95. This lateral component of movement is not expressed in the corresponding movement of the bristle carrier 52. Loss of this lateral component of movement is due to the pinned engagement between the distal end of the drive ribbon 95 and the bristle carrier 52 shown in FIG. 8. Besides this pinned arrangement, and as previously noted, it will be appreciated that other types of attachment may be utilized. For example, it may in certain applications be preferred to employ a "snap-on"

connection between the distal end of the drive ribbon 95 and the bristle carrier 52. This approach is generally preferable over techniques involving separate pins and other fastening components.

Another aspect of the present invention relates to the design of the drive ribbon 95. The drive ribbon is relatively small in terms of its cross-sectional area. Although the drive ribbon cross-sectional shape may be in a variety of forms including but not limited to round, off-round, triangular, elliptical, square, rectangular, circular, non-circular and oval for instance, the cross-sectional shape is essentially matched to the cross-sectional shape of the channel defined within neck 40, as shown in FIG. 7. Thus, if the channel in neck 40 has a rectangular cross-sectional shape, then preferably, so does the cross-section of the drive ribbon 95. Alternatively, the cross-sectional shape of the channel defined in the neck 40 may be tailored depending upon the cross-sectional shape of the drive ribbon 95. Details of preferred cross-sectional configurations for cavities defined in necks of preferred embodiment toothbrushes are described herein.

It is preferred that the cross-sectional shapes of the channel defined in the neck 40 and of the drive ribbon 95 be matched so that the degree of flexure in the drive ribbon 95 upon application of compressive force is minimized. Referring to FIGS. 5–9, it will be appreciated that upon rotation of drive gear 93, a reciprocating motion will be imparted to the drive ribbon 95. That motion will include a "push" or compressive stroke in which the drive ribbon 95 is pushed away from the motor 90, and a "pull" or tensile stroke in which the drive ribbon 95 is pulled toward the motor 90. The material forming the drive ribbon 95, described in greater detail herein, has sufficient strength to transfer the tensile force applied to the drive ribbon 95 by the gear 93 and does not significantly flex or undergo dimensional distortion. However, upon application of a compressive force by gear 93, the relatively small cross-section of the drive ribbon 95 may permit the ribbon to flex or bend relative to the channel of the neck. As will be appreciated, this is undesirable. Furthermore, bending of the ribbon 95 is an indication of inefficient transfer or loss of energy to the movable bristle carrier 52 engaged at the other end of the drive ribbon 95. Accordingly, it is preferred to appropriately size and configure the interior span or opening of the channel defined within the neck 40 so as to prevent or minimize flexure of the drive ribbon 95 relative to the channel of the neck, although it will be appreciated that the ribbon is still capable of flexing with, versus relative to, the neck during use.

In addition to matching the neck channel configuration to the cross-sectional shape of the drive ribbon 95, it is also preferred to size the drive ribbon 95 such that its outer surface is in relatively close proximity to the interior wall of the channel defined in neck 40. Preferably, the average distance between the outer surface of the drive ribbon 95 and the interior wall of the neck channel, is from about 0.1 mm to about 1 mm and more preferably from about 0.3 mm to about 1 mm. The distance between the outer surface of the drive ribbon 95 and the interior wall of the neck channel can be greater if a bushing is provided about the drive ribbon 95, in which case the average distance can be up to about 10 mm. It will be appreciated that preferably, the drive ribbon 95 has a uniform cross-section across its length. However, the present invention includes embodiments in which the drive ribbon 95 has a cross-sectional configuration that is non-uniform and varies at different locations along the length of the drive ribbon 95.

The drive ribbon 95 may be formed from a variety of materials. Preferably, the drive ribbon 95 is formed from a polymeric material that exhibits sufficient strength to transfer power from the motor to one or more movable bristle carriers 52 disposed on the head of the toothbrush 10 and which, when formed into a thin ribbon, can flex with the flexible neck. Examples of preferred polymeric materials include, but are not limited to, self-lubricating materials such as Celcon™ acetal copolymer (polyoxymethylene (POM)) manufactured by Ticona, Inc., polymeric materials such as ABS, nylon, PPE, POM (a polyoxymethylene copolymer), and Delrin™ acetal resins available from DuPont™; and metals such as steel and aluminum. The most preferred material for forming the drive ribbon 95 is Celcon™. It is also contemplated to utilize other materials for forming the drive ribbon 95. Furthermore, it may be desirable to provide a low friction coating on the exterior surface of the drive ribbon 95 to minimize friction between that component and the interior walls of the channel defined within the neck 40.

While a reciprocating ribbon 95 has been illustrated herein, it will be appreciated that a flexible shaft that rotates, ocillates, or undergoes an orbital motion could be provided within the flexible neck 40. For example, a flex shaft, such as that formed by a group of wire strands helically wound about a wire core, can be used in place of the ribbon to transmit motion to the movable bristle carrier 52. Further while a FIGS. 5 to 9 illustrate one drive mechanism for transmitting motion to a movable bristle carrier, a wide array of drive mechanisms, drive motor and gearing configurations may be adapted and suitable for use with the present invention. While the toothbrush 10 has been illustrated with a flexible neck that is formed integrally with the toothbrush handle, it is contemplated that the neck (or head) might be releasably attached to the toothbrush 10, as is known in the art.

In addition to selecting a certain cross-sectional configuration for a channel defined within a neck, based upon the cross-sectional shape of the drive ribbon or shaft, or vice-versa; the channel cross-section may either depend upon or influence the selection of the cross-section for the neck. For example, by appropriately selecting the cross-sectional shape and dimensions of the neck, the channel configuration, and the orientation of these shapes relative to each other, varying degrees of directional stiffness or flexibility may be imparted to the neck and brush head in combination with the polymer blends disclosed herein or other elastomeric or soft polymers.

Figure 10:
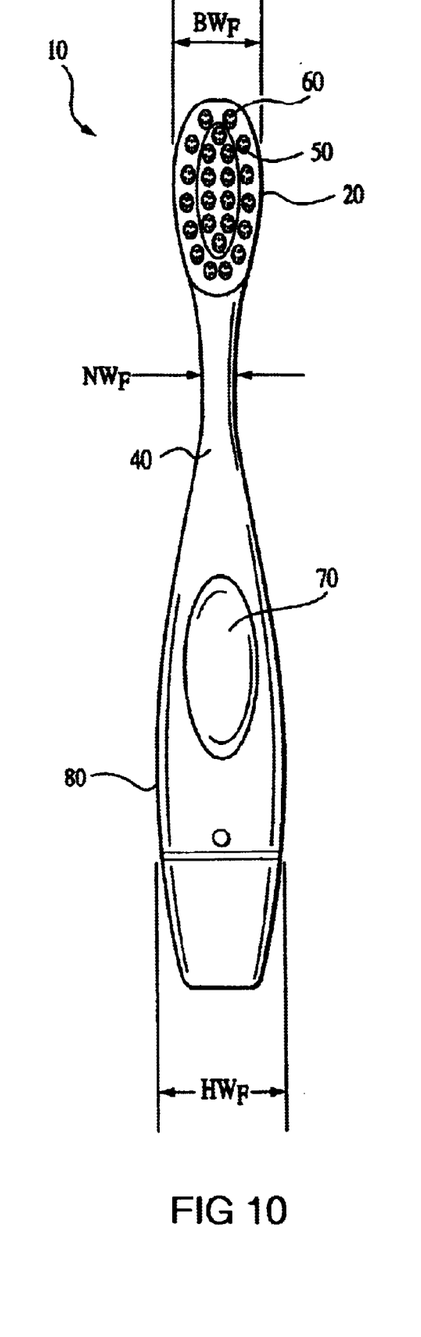
FIG. 10 is a front elevational view of the toothbrush of FIG. 1.
Figure 11:
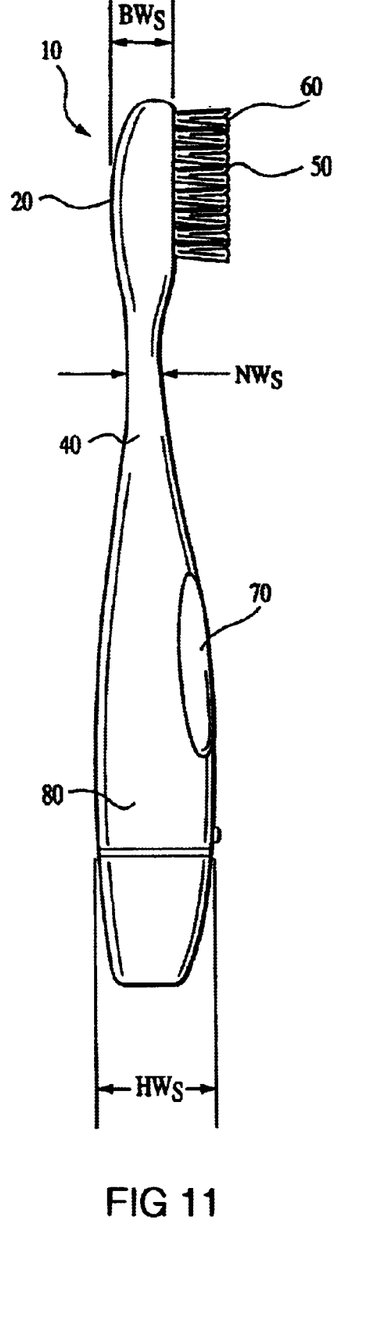
FIG. 11 is a side elevational view of the toothbrush of FIG. 1.

Generally, regions of reduced wall thickness are provided along the neck and/or neck region of the toothbrushes. The preferred embodiment toothbrush 10 features a relatively small head 20 and neck 40 relative to the size of its main body or handle 80. The minimum frontal width of the preferred embodiment toothbrush 10 as measured in the region of the neck 40, designated as $NW_F$, ranges from about 5 mm to about 12 mm, and preferably from about 6 mm to about 9 mm. This span or dimension is approximately 15% to about 55%, and preferably from about 18% to about 41%, of the maximum frontal width designated as $HW_F$ of the body or handle 80. This is illustrated in FIG. 10. The maximum frontal width of the brush head 20, designated as $BW_F$, ranges from about 10 mm to about 16 mm, and preferably from about 7 mm to about 9 mm. This span or dimension is approximately 31% to about 73%, and preferably from about 22% to about 41% of the maximum frontal width $HW_F$ of the handle or body 80. Similarly, the minimum side width of the neck 40, designated as $NW_S$ in FIG. 11, ranges from about 5 mm to about 12 mm, and preferably from about 6 mm to about 9 mm. This side span $NW_S$, expressed as a proportion of the maximum side width of the handle or body 80, designated as $HW_S$, ranges from about 12% to about 40%, and preferably from about 15% to about 30%. The maximum side width of the handle or body 80, $HW_S$, is illustrated in FIG. 11. The maximum side width of the brush head 20, designated as $BW_S$, and exclusive of any thickness dimension from one or more bristle carriers, ranges from about 6 mm to about 12 mm, and preferably from about 7 mm to about 9 mm. This span or dimension is approximately 15% to about 40%, and preferably from about 17% to about 30% of the maximum side width $HW_S$ of the handle or body 80. It will be understood that the present invention includes embodiments in which the dimensions and proportions of the brush head and neck are greater or lesser than the noted body or handle portions.

FIGS. 12–20 are cross-sectional views taken along the neck of various electric toothbrushes in accordance with the present invention. Specifically, each of these cross-sections illustrate various exemplary cross-sectional configurations for the shape of the neck and the interior channel defined within the neck within which the drive ribbon or shaft resides. It will be appreciated that in all of these figures, a drive ribbon or shaft, although not shown, is disposed within the channel defined in the neck.

Figure 12:
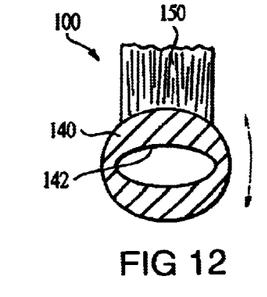
FIGS. 12 to 20 are cross-sectional views of various toothbrush neck configurations.
Figure 13:
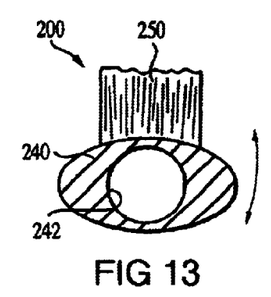
Figure 14:
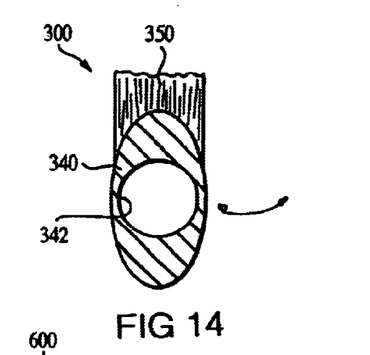
Figure 15:
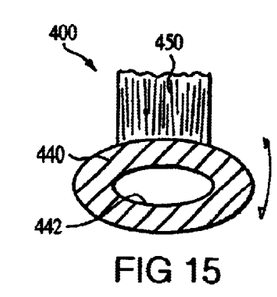
Figure 16:
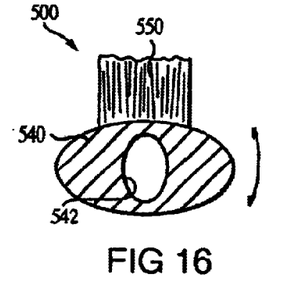
Figure 17:
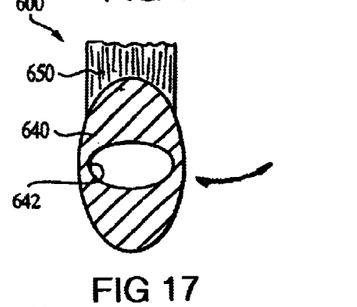
Figure 18:
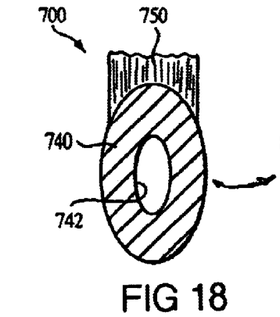
Figure 19:
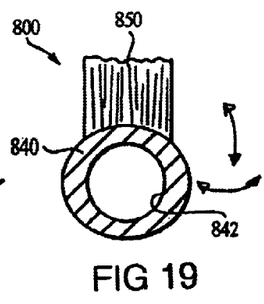
Figure 20:
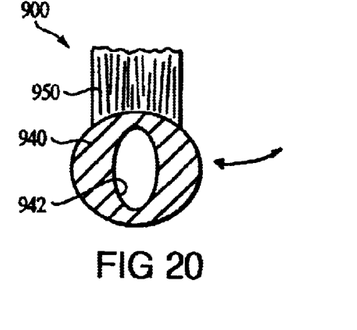

By way of example, FIG. 12 illustrates a toothbrush 100 comprising a neck 140, a channel 142 defined therein, and a plurality of bristles 150 on a brush head (not shown). In this embodiment, the channel cross-sectional shape is elliptical or oval and oriented such that the major axis of the channel cross-sectional shape is generally perpendicular to the orientation of the bristles 150. And, the cross-sectional shape of the neck 140, i.e. of the outer surface of the neck 140, is generally round or circular. The primary direction of bending of this shape is illustrated by the double headed arrow. The minimum wall thickness of the neck, which in this case is located at the side surfaces of the neck, is preferably between about 1 mm and about 3 mm, although this value can be varied depending on the polymer or polymer blend used to form the neck. This cross-sectional shape can be used to control the direction of bending of the flexible neck so that it primarily bends in a rearward or forward direction as shown by the arrow. In contrast, FIG. 14 illustrates a flexible neck that primarily bends in lateral or side-to-side direction.

FIGS. 13 to 20 illustrate further embodiments of the toothbrush comprising a neck, a channel defined therein, and bristles extending from a brush head (not shown). The cross-sectional shape of the channels (e.g., 242, 342, 442, 542, 642, 742, 842, 942) vary from circular to elliptical or oval. The major axis of the neck cross-sectional shape may generally be perpendicular to the orientation of the bristles (e.g., FIG. 16) or generally parallel to the orientation of the bristles (e.g., FIG. 17). The major axis of the channel cross-sectional shape may be generally perpendicular to the major axis of the neck cross-sectional shape (e.g., FIG. 16) or generally parallel to the major axis of the neck cross-sectional shape (e.g., FIG. 15). The primary direction of bending of each cross-sectional shape is illustrated by a double headed arrow. The minimum wall thickness of the neck is preferably between about 1 mm and about 3 mm, although this value can be varied depending on the polymer used to form the neck and the desired flexibility. It will be understood that the present invention includes neck and channel cross-sectional shapes, combinations of shapes, and orientations in addition to those shown in the referenced figures.

The extent of stiffness, rigidity, or flexibility of the neck may be controlled by appropriate selection of the shape and orientation of the neck and the shape and orientation of the channel defined within the neck in combination with the polymer selection. Neck cross-sections having regions of wall thickness that vary at different locations along the cross-section, will impart stiffness-altering properties to the neck so, for example, a neck might bend with a compound radius of curvature. Thus, wall regions having relatively large thicknesses will be more resistant to bending and flexure at that region, than for instance wall regions having lesser thicknesses or relatively thin walls. Additionally, the stiffness, rigidity, or flexibility may be controlled by appropriate selection of the material(s) used in forming the neck as previously discussed.

Figure 21:
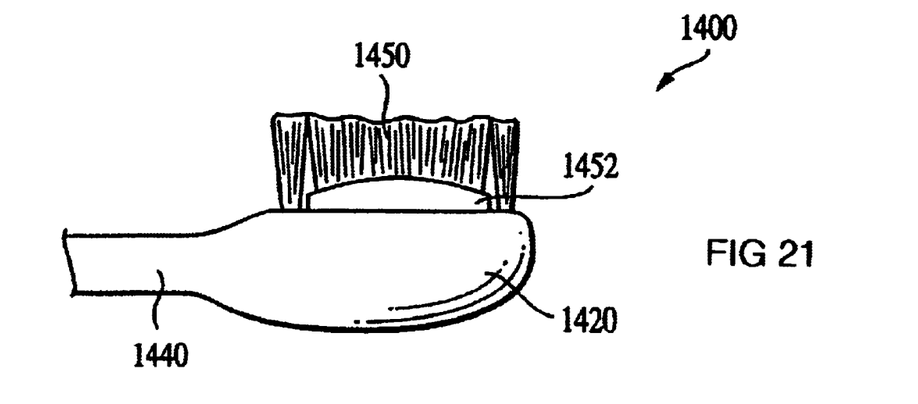
FIGS. 21 to 23 are side elevational views of some toothbrush heads suitable for use with a flexible neck.
Figure 22:
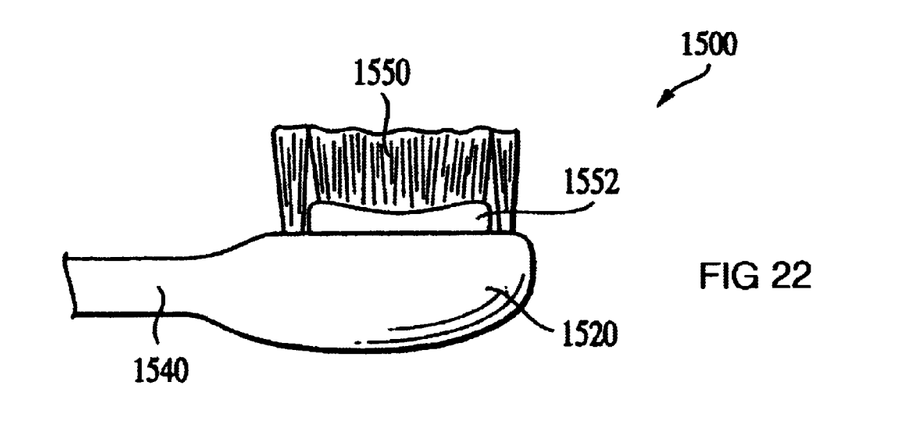
Figure 23:
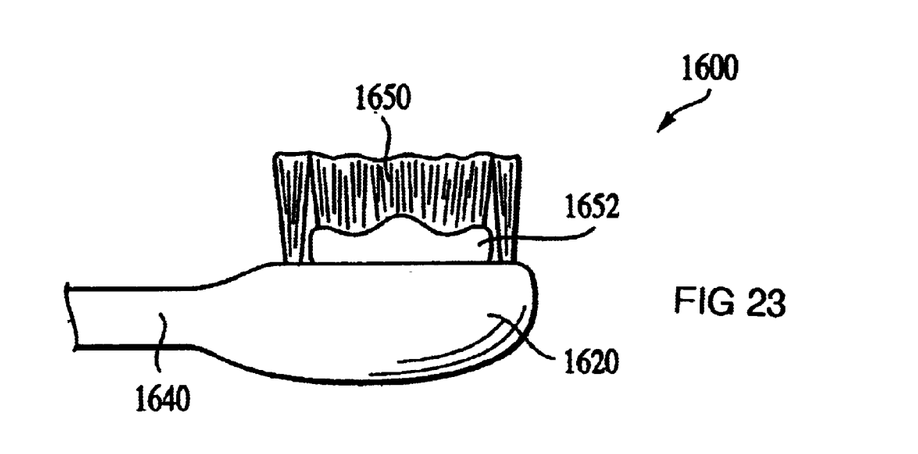
Figure 24:
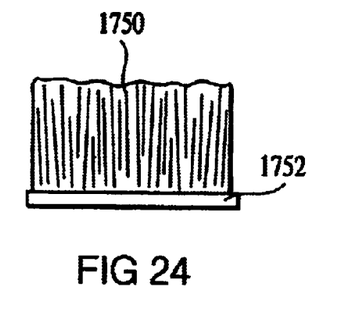
FIG. 24 is a side elevational view of movable bristle carrier suitable for use with a flexible neck.
Figure 25:
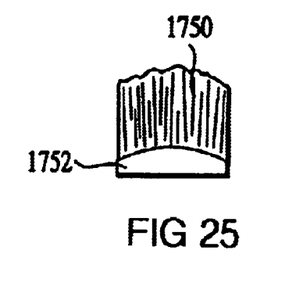
FIG. 25 is an end view of the movable bristle carrier of FIG. 24.

FIGS. 21 to 23 illustrate partial side views of various toothbrush heads suitable for use with the present invention. Each of these toothbrush heads utilize bristle carriers having certain configurations as described herein that can be used to alter the stiffness of the bristles to change or enhance the effect of the flexible neck. FIGS. 21 to 26 illustrate toothbrushes comprising a brush head (e.g., 1420) and a neck (e.g., 1440). A movable bristle carrier (e.g., 1452) is provided on the brush head. A plurality of bristles (e.g., 1450) are provided on the outer region of the brush head and bristle carrier. The movable bristle carrier can be provided with a convex, concave, irregular, outer surface when viewed from either the side.

Figure 26:
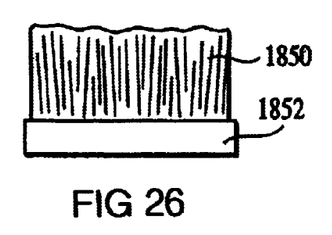
FIG. 26 is a side elevational view of movable bristle carrier suitable for use with a flexible neck.
Figure 27:
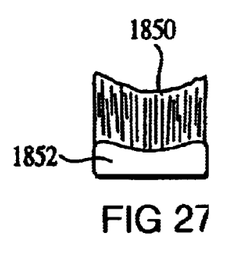
FIG. 27 is an end view of the movable bristle carrier of FIG. 26.
Figure 28:
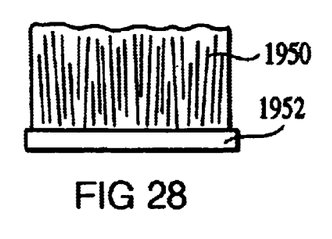
FIG. 28 is a side elevational view of movable bristle carrier suitable for use with a flexible neck.
Figure 29:
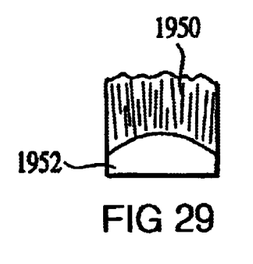
FIG. 29 is an end view of the movable bristle carrier of FIG. 28.

Referring to the various bristle carriers illustrated in FIGS. 21 to 29, it can be seen that the profile or configuration of the outwardly facing surface of the carrier, generally referred to herein as a "brush-facing" surface, may be in a variety of forms and shapes. One particularly preferred shape is a concave shape. A concave side configuration such as shown in FIG. 22, or a concave end configuration such as shown in FIG. 27 may be utilized. Specifically, a concave side configuration refers to a concave shape when viewed in a direction generally perpendicular to a longitudinal axis of the toothbrush. A concave end configuration refers to a concave shape when viewed in a direction generally parallel to and collinear with a longitudinal axis of the toothbrush. The definitions for convex side and convex end shapes are analogous. It is further contemplated to provide a compound concave surface that is concave with respect to both side and end views of the bristle carrier. A concave shape promotes the retention of dentifrice or polishing material that may be used during brushing and can advantageously alter the stiffness of bristles. Likewise, a convex surface such as shown in FIGS. 22, 26, and 30, promotes the dissipation of dentifrice in the region of the bristles along the brush head.

The formation of the brush body, i.e., head, neck and handle, as a one-piece mixture of polymer materials according to the present invention provides the advantage of true, multi-directional flexibility. In other words, the head portion of the toothbrush of the present invention can be displaced and oriented in any direction with respect to the handle portion of the brush with ease. This is in contrast to conventional brushes, in which the head has at best only a uni-directional flexing capability with respect to the handle and then only if a force significantly greater than a toothbrushing force is applied. In contrast, the present invention provides a neck that is extremely flexible, in one or more directions, under small forces.

The flexible neck can also act to buffer excessive force on the teeth and gums that may be exerted by a user. As previously noted, application of excessive force during brushing is deleterious to the gums. Accordingly, by appropriate selection of the polymers forming the neck of the preferred embodiment toothbrush described herein, application of excessive force can be prevented.

The present invention may utilize features, aspects, components, materials, and characteristics from one or more of the following published patent applications or issued patents: WO 01/29128; U.S. Pat. No. 6,000,083; U.S. Des. Pat. 432,312; U.S. Des. Pat. 433,814; U.S. Pat. No. 6,178,579; U.S. Pat. No. 6,189,693; U.S. Pat. No. 6,311,837; U.S. published patent application 2002/0032941; U.S. Pat. No. 6,360,395; and U.S. Pat. No. 6,371,294; all of which are hereby incorporated by reference.

The foregoing description is, at present, considered to be the preferred embodiments of the present invention. However, it is contemplated that various changes and modifications apparent to those skilled in the art, may be made without departing from the present invention. Therefore, the foregoing description is intended to cover all such changes and modifications encompassed within the spirit and scope of the present invention, including all equivalent aspects.

What is claimed is:

1. An electric toothbrush, comprising:
   a handle having a cavity;
   a head;
   a flexible neck extending between said handle and said head, said flexible neck formed, at least in part, from a blend comprising a first and a second polymer or a mixture comprising a first and a second polymer.
   a movable bristle carrier disposed on said head;
   a motor disposed within said cavity;
   a shaft disposed within said flexible neck and operatively connected to said movable bristle carrier and to said motor;
   wherein said head and said flexible neck comprise a channel, said channel extending through said flexible neck and into said head; and
   wherein said neck can flex at least about 5 degrees when a force of at least about 4 N is applied to said head.

2. The electric toothbrush of claim 1, wherein said first polymer is selected from the group consisting of polypropylene, polystyrene, acrylonitrile-styrene copolymer, and cellulose acetate-propionate, and mixture thereof.

3. The electric toothbrush of claim 2, wherein the weight ratio of said first polymer to said second polymer is from about 95:5 to about 30:70.

4. The electric toothbrush of claim 1, wherein said second polymer is selected from the group consisting of a thermoplastic elastomer, a thermoplastic olefin, a soft thermoplastic polyolefin, and an elastomer.

5. The electric toothbrush of claim 4, wherein the Shore A hardness of said second polymer is from about 25 to about 85.

6. The electric toothbrush of claim 4, wherein the Shore A hardness of said second polymer is from about 45 to about 65 and the weight ratio of said first polymer to said second polymer is from about 80:20 to about 50:50.

7. The electric toothbrush of claim 1, wherein said neck is sufficiently flexible to permit said head to be reversible laterally displaced an angle of from about 25 degrees to about 5 degrees, with respect to a longitudinal axis of said toothbrush prior to being displaced.

8. The electric toothbrush of claim 1, wherein said neck is sufficiently flexible to permit said head to be reversible rearwardly displaced an angle of from about 15 degrees to about 5 degrees with respect to a longitudinal axis of said toothbrush prior to being displaced.

9. The electric toothbrush of claim 1, wherein said neck is sufficiently flexible to permit said head to be reversible rearwardly displaced an angle of from about 15 degrees to about 5 degrees with respect to a longitudinal axis of said toothbrush prior to being displaced.

10. The electric toothbrush of claim 1, wherein said shaft is a flexible ribbon.

11. The electric toothbrush of claim 1, wherein said channel has an elliptical cross-section shape.

12. The electric toothbrush of claim 1, wherein said neck has an elliptical cross-section shape.

13. The electric toothbrush of claim 1, wherein said neck is sufficiently flexible to permit said head to be laterally displaced an angle of from about 15 degrees to about 5 degrees with respect to a longitudinal axis of said toothbrush prior to being displaced.

14. The electric toothbrush of claim 1, wherein the Shore A hardness of said second polymer is from about 25 to about 45 and the weight ratio of said first polymer to said second polymer is from about 90:10 to about 60:3550.

15. The electric toothbrush of claim 1, wherein the Shore A hardness of said second polymer is from about 65 to about 85 and the weight ratio of said first polymer to said second polymer is from about 70:30 to about 40:60.

16. The electric toothbrush of claim 1, wherein said shaft reciprocates.

17. The electric toothbrush of claim 1, wherein a substantially entire portion of said neck is formed from said first polymer and said second polymer.

18. An electric toothbrush, comprising:
    a handle having a cavity,
    a head;
    a flexible neck extending between said handle and said head, said flexible neck comprising at least a first and second polymer;
    a movable bristle carrier disposed on said head;
    a motor disposed within said cavity;
    a reciprocating flexible shaft disposed within said flexible neck and operatively connected to said movable bristle carrier and to said motor;
    wherein said head and said flexible neck comprise a channel, said channel extending through said flexible neck and into said head;
    wherein said neck can flex at least about 5 degrees when a force of at least about 4 N is applied to said head.

19. The electric toothbrush of claim 18, wherein said first polymer is selected from the group consisting of polypropylene, polystyrene, acrylonitrile-styrene copolymer, and cellulose acetate-propionate, and mixtures thereof.

20. The electric toothbrush of claim 19, wherein said second polymer is selected from the group consisting of a thermoplastic elastomer, a thermoplastic olefin, a soft thermoplastic polyolefin, and an elastomer.

21. The electric toothbrush of claim 20 wherein said neck is sufficiently flexible to permit said head to be reversibly rearwardly displaced an angle of from about 15 degrees to a bout 5 degrees with respect to a longitudinal axis of said toothbrush prior to being displaced.

22. The electric toothbrush of claim 21, wherein the Shore A hardness of said second polymer is from about 25 to about 85.

23. The electric toothbrush of claim 21, wherein the Shore A hardness of said second polymer is from about 45 to about 65 and the weight ratio of said first polymer to said second polymer is from about 80:20 to about 50:50.

24. The electric toothbrush of claim 18, wherein the Shore A hardness of said second polymer is from about 25 to about 45 and the weight ratio of said first polymer to said second polymer is from about 90:10 to about 60:35.

* * * * *